(12) United States Patent
Kikuchi

(10) Patent No.: US 11,203,114 B2
(45) Date of Patent: Dec. 21, 2021

(54) MANIPULATOR

(71) Applicant: OLYMPUS CORPORATION, Tokyo (JP)

(72) Inventor: Yuki Kikuchi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 103 days.

(21) Appl. No.: 16/710,088

(22) Filed: Dec. 11, 2019

(65) Prior Publication Data

US 2020/0114505 A1     Apr. 16, 2020

Related U.S. Application Data

(63) Continuation of application No. PCT/JP2017/021932, filed on Jun. 14, 2017.

(51) Int. Cl.
*B25J 9/10* (2006.01)
*A61B 34/00* (2016.01)
(Continued)

(52) U.S. Cl.
CPC .............. *B25J 9/104* (2013.01); *A61B 34/71* (2016.02); *B25J 9/065* (2013.01); *A61B 2017/2939* (2013.01)

(58) Field of Classification Search
CPC  B25J 9/104; B25J 9/065; A61B 34/71; A61B 1/0051; A61B 1/0055; A61B 1/008; A61B 2017/0069
See application file for complete search history.

(56) References Cited

U.S. PATENT DOCUMENTS 7,699,835 B2 *  4/2010  Lee ................... A61B 34/35
                                                   606/1
7,854,738 B2 * 12/2010  Lee ................... A61B 34/35
                                                   606/130
(Continued)

FOREIGN PATENT DOCUMENTS

EP      3085324 A1   10/2016
JP   2010-17483 A     1/2010
(Continued)

OTHER PUBLICATIONS

International Search Report dated Aug. 1, 2017 issued in PCT/JP2017/021932.

*Primary Examiner* — Bobby Rushing, Jr.
(74) *Attorney, Agent, or Firm* — Scully, Scott, Murphy & Presser, P.C.

(57) ABSTRACT

A manipulator includes an elongated portion; a bending portion coupled to a distal end of the elongated portion, the bending portion being formed by articulating a plurality of segment pieces; an end effector coupled to a distal end of the bending portion; an actuator coupled to a proximal end of the elongated portion; a first wire coupled to between the actuator and the end effector, the first wire being configured to actuate the end effector; and a second wire coupled to between the actuator and the bending portion, the second wire being configured to actuate the bending portion. Each of the plurality of segment pieces is configured to be articulated so as to be twisted with respect to a longitudinal central axis of the bending portion, and the first wire is configured to be inserted into the plurality of segment pieces so as to form a substantially twisted path.

5 Claims, 7 Drawing Sheets

(51) Int. Cl.
*B25J 9/06* (2006.01)
*A61B 17/29* (2006.01)

(56) References Cited

U.S. PATENT DOCUMENTS

| | | |
|---|---|---|
| 2010/0010309 A1 | 1/2010 | Kitagawa |
| 2011/0196419 A1 | 8/2011 | Cooper |
| 2016/0256183 A1 | 9/2016 | Cooper |
| 2016/0287346 A1 | 10/2016 | Hyodo et al. |
| 2017/0056118 A1 | 3/2017 | Cooper et al. |
| 2019/0142538 A1 | 5/2019 | Hyodo et al. |

FOREIGN PATENT DOCUMENTS

| | | |
|---|---|---|
| JP | 2010-259479 A | 11/2010 |
| JP | 2013-518665 A | 5/2013 |
| JP | 2017-512659 A | 5/2017 |
| WO | WO 2011/097095 A1 | 8/2011 |
| WO | WO 2015/093602 A1 | 6/2015 |
| WO | WO 2015/126752 A1 | 8/2015 |

* cited by examiner

MANIPULATOR

CROSS-REFERENCE TO RELATED APPLICATIONS

This is a continuation of International Application PCT/JP2017/021932 which is hereby incorporated by reference herein in its entirety.

TECHNICAL FIELD

The present invention relates to a manipulator.

BACKGROUND ART

There is known a manipulator in which an elongated portion is constituted by multiple segment pieces that are disposed in the long axis direction and adjacent segment pieces are connected to each other so as to be pivotable on multiple axes that are twisted relative to each other, and in which wires for driving an end effector at the distal end are passed through holes that penetrate the respective segment pieces in a direction parallel to the longitudinal axis so that the wires extend along the longitudinal axis (for example, see PTL 1).

CITATION LIST

Patent Literature

{PTL 1}
United States Patent Application No. 2017/0056118

According to one aspect of the present invention, there is provided a manipulator that includes an elongated portion; a bending portion coupled to a distal end of the elongated portion, the bending portion being formed by articulating a plurality of segment pieces; an end effector coupled to a distal end of the bending portion; an actuator coupled to a proximal end of the elongated portion; a first wire coupled between the actuator and the end effector, the first wire being configured to actuate the end effector; and a second wire coupled between the actuator and the bending portion, the second wire being configured to actuate the bending portion. Each of the plurality of segment pieces is configured to be articulated so as to be twisted with respect to a longitudinal central axis of the bending portion, and the first wire is configured to be inserted into the plurality of segment pieces so as to form a substantially twisted path.

DESCRIPTION OF EMBODIMENTS

A manipulator 1 according to one embodiment of the present invention will now be described with reference to the drawings.

Figure 1:
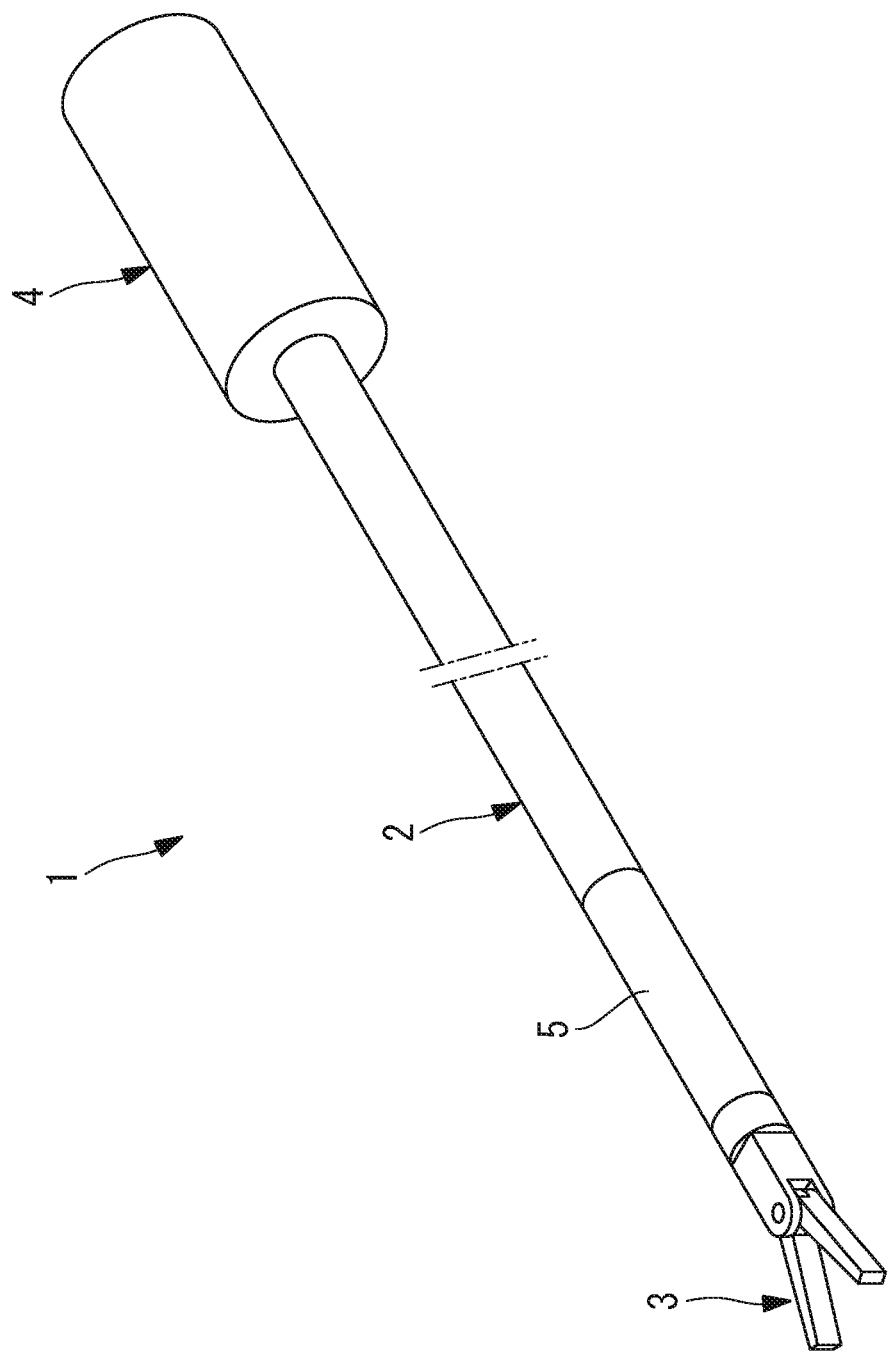
FIG. 1 is a perspective view of a manipulator according to an embodiment of the present invention.

As illustrated in FIG. 1, the manipulator 1 according to this embodiment includes an elongated portion 2, an end effector 3 disposed at a distal end of the elongated portion 2, a drive unit (actuator) 4 that is disposed at a proximal end of the elongated portion 2 and generates a driving force to be transmitted to the end effector 3, and a wire (first wire) 13 (refer to FIG. 2) that transmits the driving force generated in the drive unit 4 to the end effector 3. The end effector 3 is, for example, a grasping portion that constitutes grasping forceps.

A bending portion 5 for changing the orientation of the end effector 3 is disposed near the distal end of the elongated portion 2.

Figure 2:
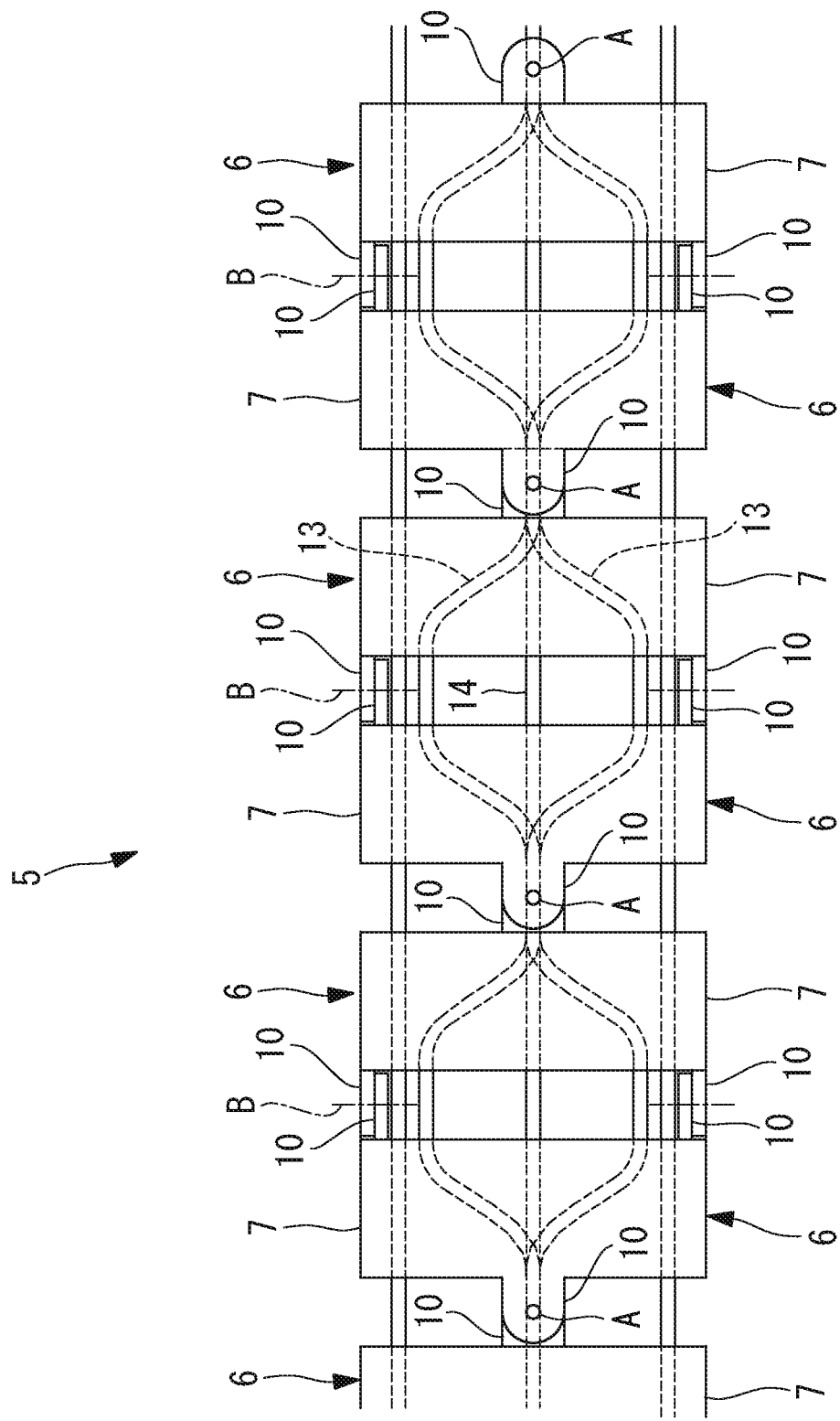
FIG. 2 is a side view of a bending portion of the manipulator illustrated in FIG. 1.
Figure 3:
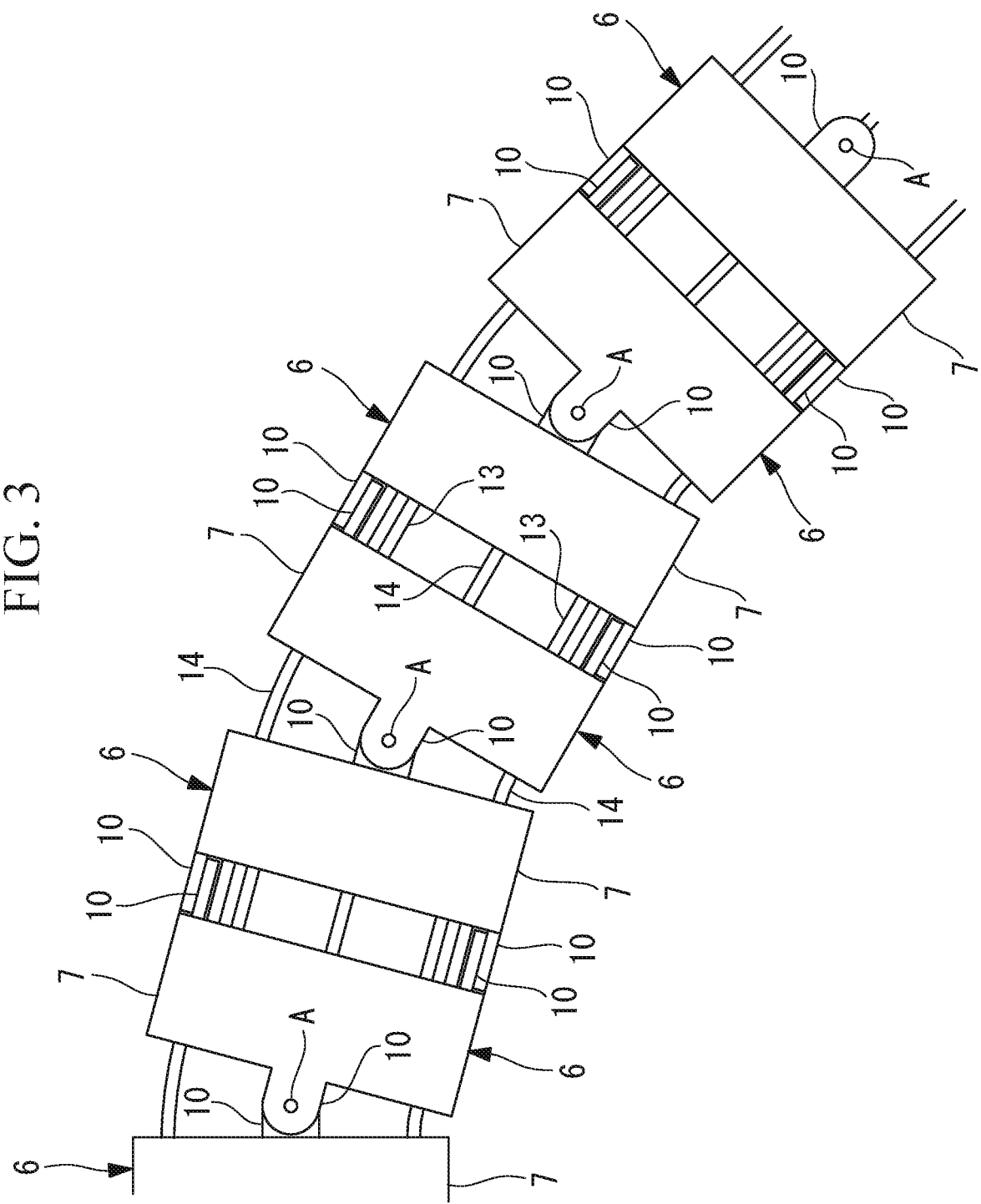
FIG. 3 is a side view of the bending portion illustrated in FIG. 2 when bent in one direction.

As illustrated in FIGS. 2 and 3, the bending portion 5 includes cylindrical segment pieces (nodal rings) 6 arranged in a direction along the center axis of the elongated portion 2, and adjacent segment pieces 6 are connected to each other so as to be pivotable on pivot axes A and B that are twisted relative to each other.

In this manner, one segment piece 6 is caused to pivot in one direction with respect to an adjacent segment piece 6 on one side and is caused to pivot in another direction with respect to an adjacent segment piece 6 on the other side. Thus, three or more consecutive segment pieces 6 constitute a bending portion 5 that can freely change the orientation of the end effector 3.

Figure 4:
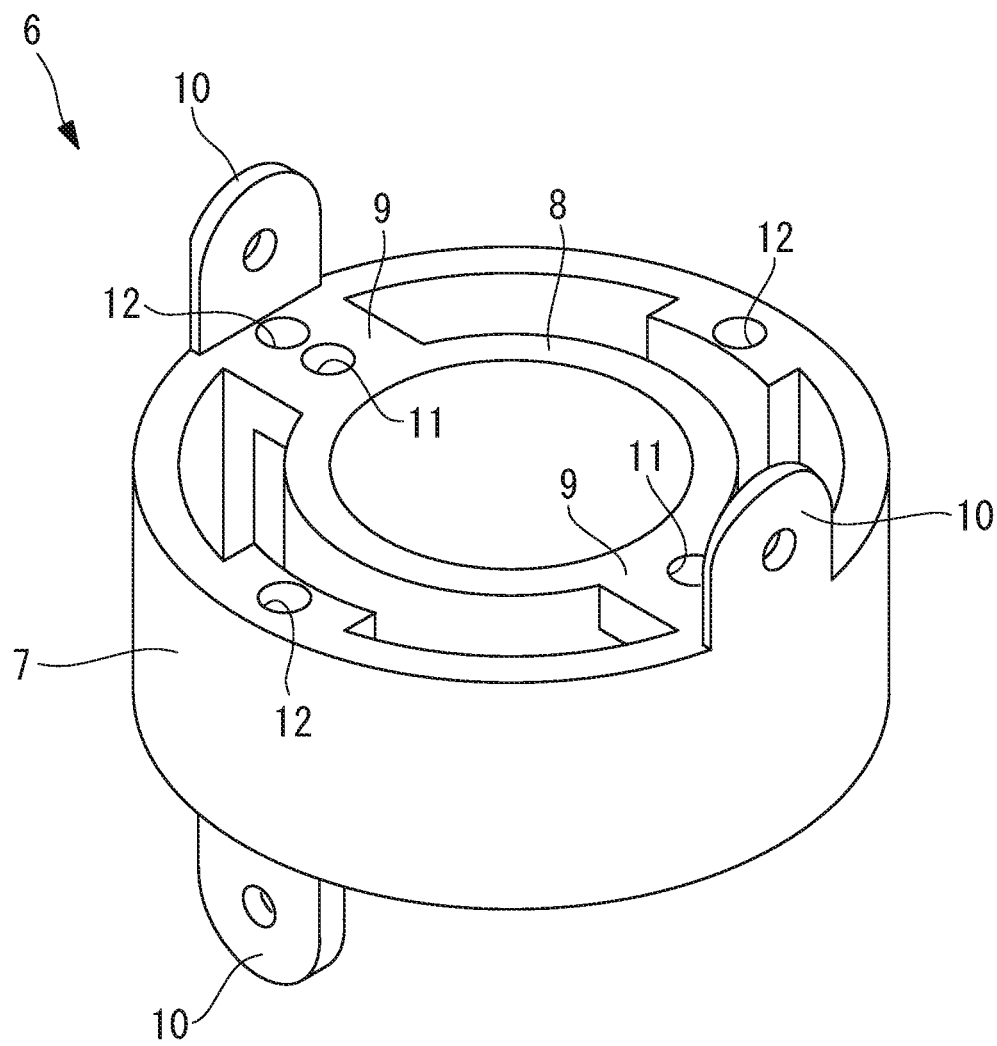
FIG. 4 is a perspective view of one example of a segment piece constituting the bending portion illustrated in FIG. 2.
Figure 5:
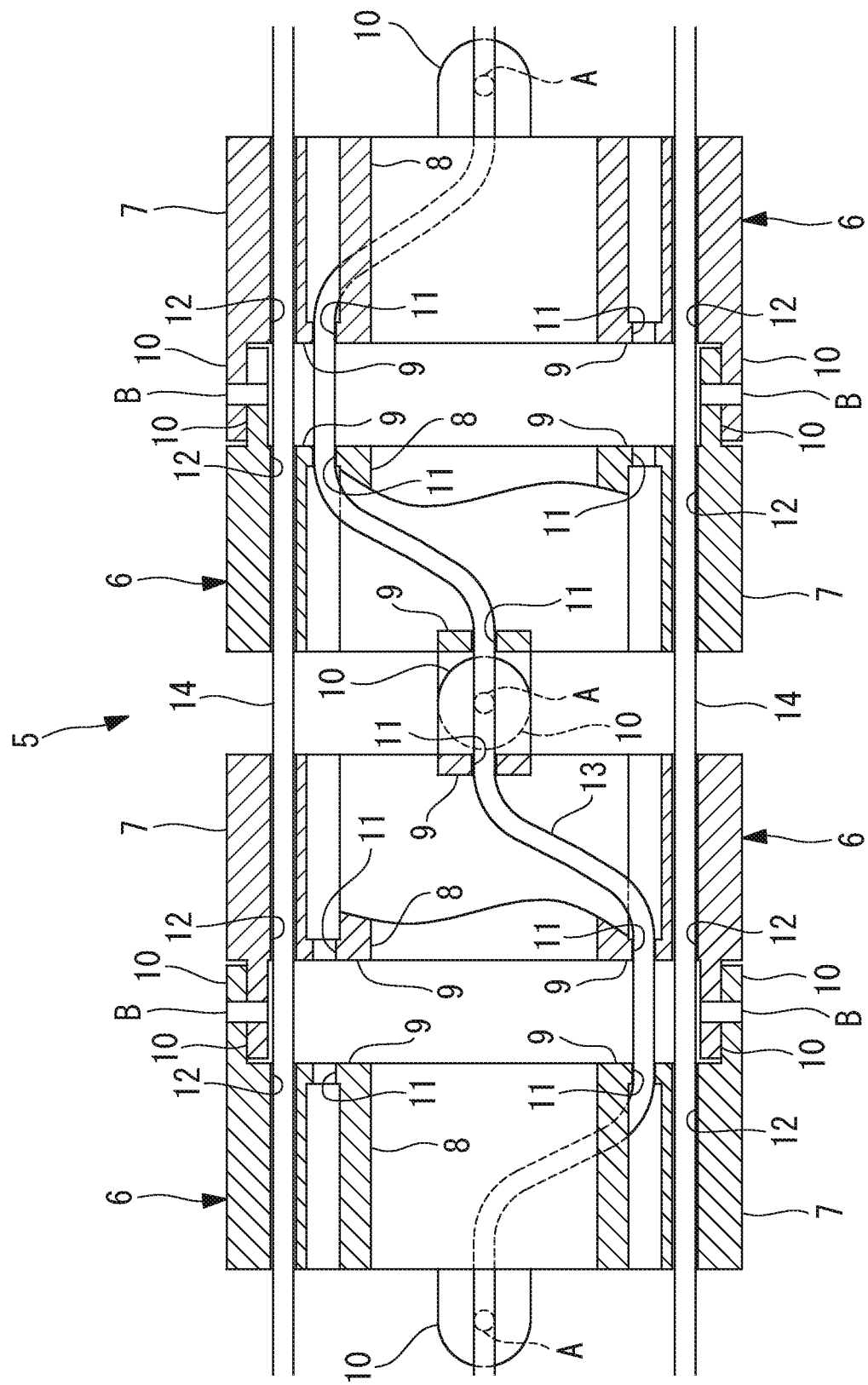
FIG. 5 is a longitudinal sectional view of a state in which four segment pieces illustrated in FIG. 4 are connected.

As illustrated in FIGS. 4 and 5, each segment piece 6 includes a cylindrical outer wall portion 7, a cylindrical inner wall portion 8 disposed on the radially inner side of the outer wall portion 7 so as to be concentric with the outer wall portion 7 with a space between the inner wall portion 8 and the outer wall portion 7, and connecting portions 9 that connect the outer wall portion 7 and the inner wall portion 8 to each other in the radial direction.

Moreover, the two ends of the segment piece 6 in the center axis direction are each provided with a pair of projecting portions 10 that face each other with the center axis therebetween so that adjacent segment pieces 6 can be connected to each other on the pivot axes A and B. The projecting portions 10 each extend in a direction along the center axis. There is a 90° phase difference in the circumferential direction between the projecting portions 10 on two ends of the segment piece 6 in the center axis direction. As a result, the two pivot axes A and B are twisted relative to each other.

As illustrated in FIG. 5, the projecting portions 10 of the two adjacent segment pieces 6 connected on the pivot axes A and B assume different radial positions so that the projecting portions 10 overlap each other in the radial direction.

The connecting portion 9 in the same phase as the corresponding projecting portion 10 is a strip-shaped portion extending in the radial direction and having a thickness in the direction along the center axis, and has a through hole (first through hole) 11 that penetrates through the connecting portion 9 in the thickness direction. Since the projecting portions 10 disposed on the two ends of each segment piece 6 are positioned such that there is a 90° phase difference therebetween, the connecting portions 9 are also arranged to have a 90° phase difference.

In the drawings, reference sign 12 denotes through holes (second through holes) through which four wires (second wires) 14 for bending the bending portion 5 by means of tension are passed.

In this embodiment, a wire 13 that has passed through a through hole 11 in one connecting portion 9 of the segment piece 6 is caused to pass through a through hole 11 of another connecting portion 9 having a phase 90° different from the aforementioned connecting portion 9. Since the projecting portions 10 of the adjacent segment pieces 6 connected on the same pivot axes A and B are in the same phase, the connecting portions 9 are also in the same phase. Thus, the wire 13 is passed through two connecting portions 9 of the adjacent segment pieces 6 in the same phase, and is thereby caused to pass through the positions that intersect the pivot axes A and B between these connecting portions 9.

Moreover, as illustrated in FIG. 5, since the wire 13 is sequentially passed through the through holes 11 arranged to assume positions with a phase shift in the same direction, the wire 13 takes a helical form turning in one direction about the center axis.

An operation of the manipulator 1 according to this embodiment having the aforementioned structure will now be described.

Since the manipulator 1 of this embodiment includes a bending portion 5 in which the segment pieces 6 arranged in the center axis direction are connected so that the adjacent segment pieces 6 are pivotable about the pivot axes A and B that are twisted relative to each other, the orientation of the end effector 3 disposed at the distal end of the elongated portion 2 can be freely changed by adjusting the pivot angles about the pivot axes A and B of the bending portion 5.

When a tension is applied to the wire 13 by actuating the drive unit 4, the tension is transmitted to the end effector 3 via the wire 13, and the end effector 3 is actuated.

Figure 6:
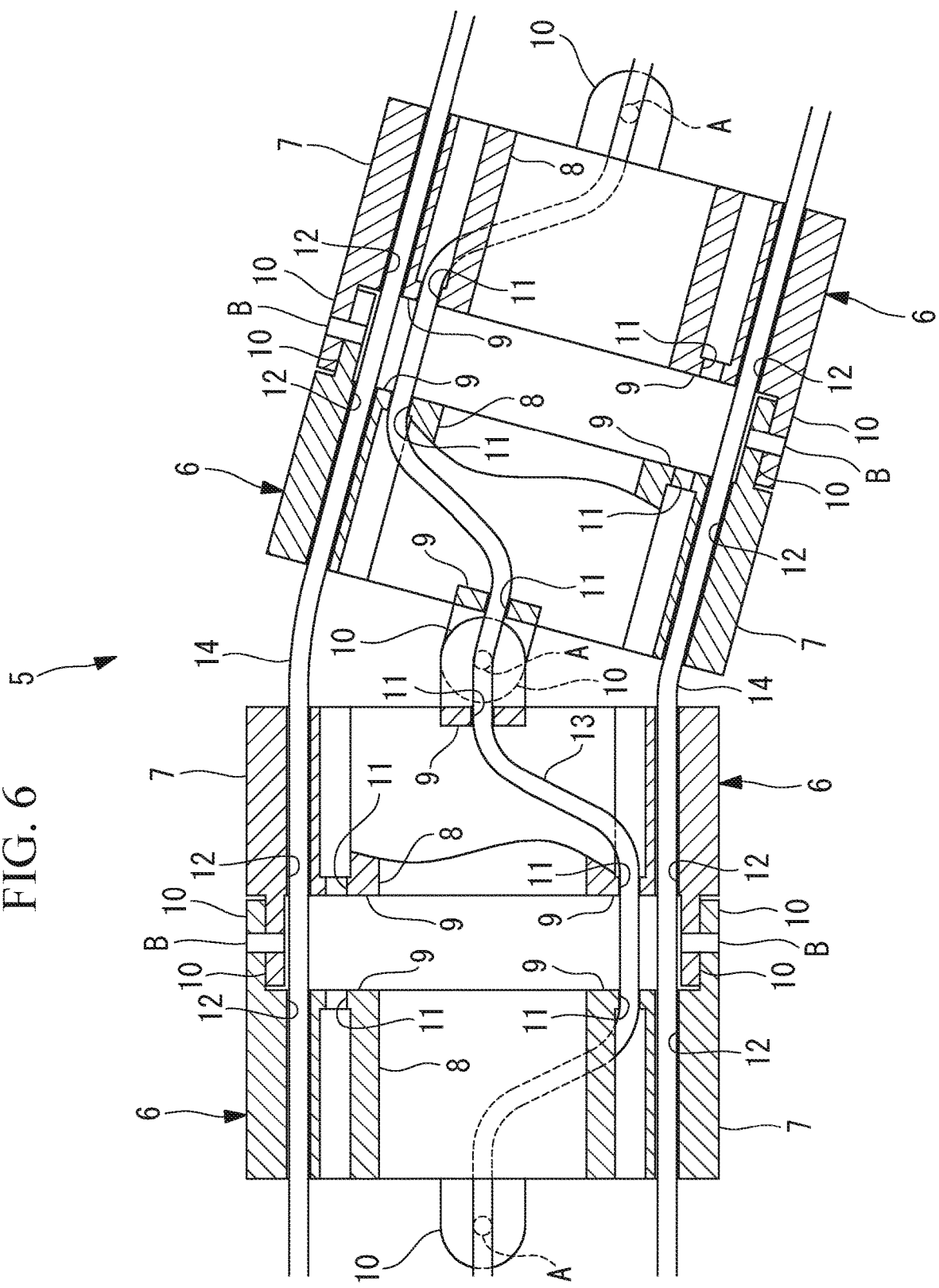
FIG. 6 is a diagram illustrating displacement of wires when the segment pieces illustrated in FIG. 5 pivot.

In this case, since the wire 13 is caused to pass through positions that intersect the pivot axes A and B, the displacement caused by pivoting is absorbed since the wire 13 is bent as illustrated in FIG. 6 even when the adjacent segment pieces 6 are relatively pivoted about the pivot axes A and B.

In other words, a movable portion of the wire 13 formed by bending the bending portion 5 is disposed only near each of the pivot axes A and B, and other portions of the wire 13 do not undergo displacement. Thus, even when the segment pieces 6 are relatively pivoted about all of the pivot axes A and B, only a bending force acts on the wire 13, and a tension or a compressive force does not act on the wire 13. Thus, the generation of a difference in path length between the wires 13 can be effectively prevented.

In other words, even when the orientation of the end effector 3 is changed by pivoting the segment pieces 6 in the bending portion 5 on the respective pivot axes A and B, an unnecessary tension does not act on the wires 13 for driving the end effector 3. Thus, there is an advantage in that unintentional movement of the end effector 3 can be eliminated, and the operability can be improved.

In addition, in this embodiment, the drive unit 4 may be a unit that is driven by a motor or a unit that is driven by manual operation.

In this embodiment, since the wires 13 for driving the end effector 3 are disposed along cylindrical gaps between the outer wall portion 7 and the inner wall portion 8, which are formed to have a double-tube shape, continuous spaces can be secured near the center axis on the inner side of the inner wall portion 8, and, thus, these continuous spaces can be effectively used to route wires and tubes that connect to the end effector 3 without being obstructed by the wires 13.

In this embodiment, a case in which the phases of the pivot axes A and B arranged on the both ends in the direction along the center axis of each segment piece 6 are shifted 90° from each other is described as an example. However, the arrangement is not limited to this, and the phase may have any magnitude.

Figure 7:
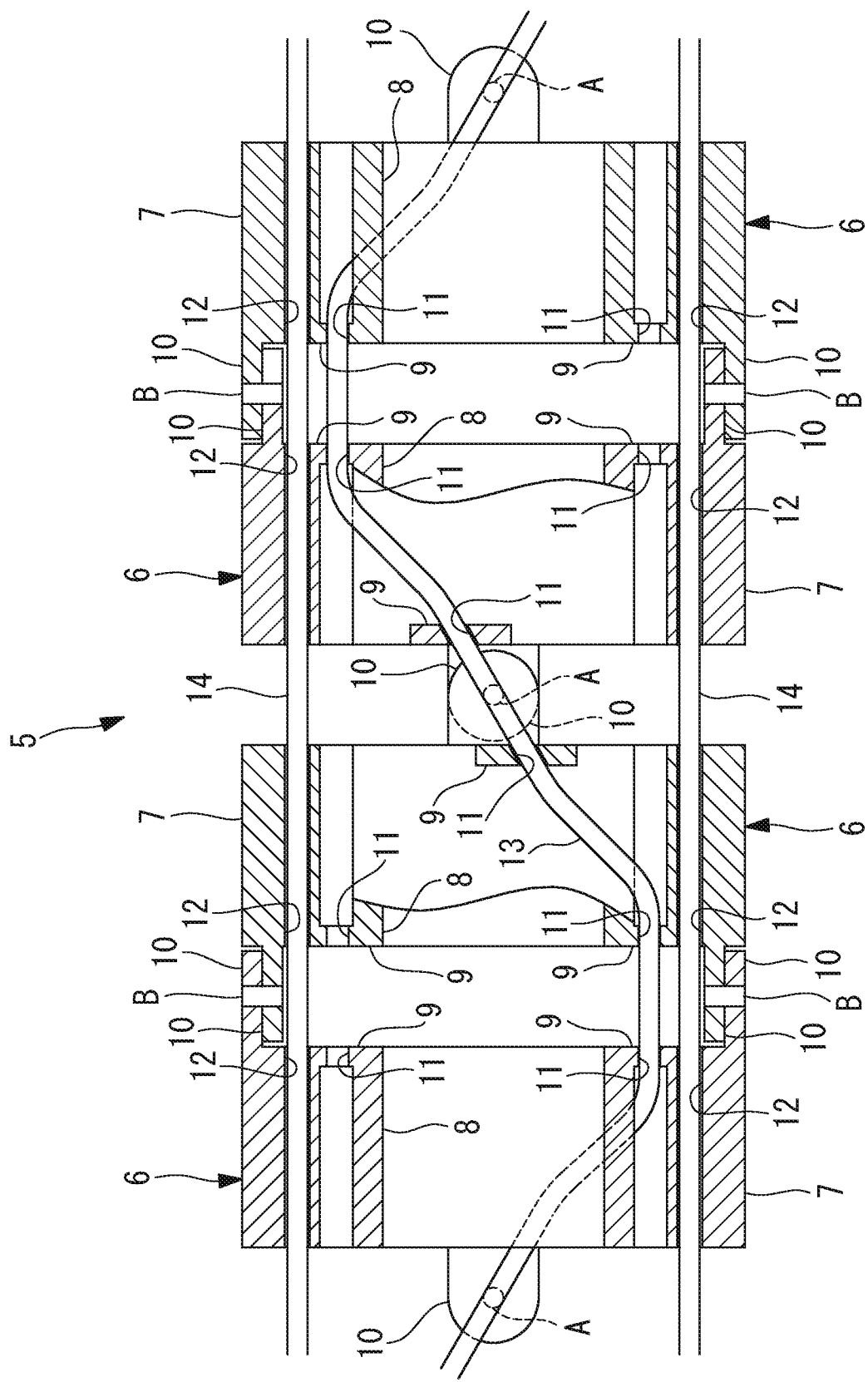
FIG. 7 is a longitudinal sectional view of a modification of the bending portion illustrated in FIG. 2.

Moreover, the case in which the through holes 11 that allow the wires 13 to pass are formed in the connecting portions 9 so as to extend parallel to the center axis is described as an example. Alternatively, as illustrated in FIG. 7, the through holes 11 may penetrate in a direction slanted toward one direction in the circumferential direction. As long as the wires 13 pass through the positions that intersect the pivot axes A and B, the effect of eliminating the generation of a difference in path length remains the same. This provides an advantage in that the wires 13 can be smoothly arranged into a helical form by having the wires 13 pass in a slanted manner.

The above-described embodiment also leads to the following invention.

According to one aspect of the present invention, there is provided a manipulator that includes an elongated portion; an end effector disposed at a distal end of the elongated portion; a drive unit disposed at a proximal end of the elongated portion; and one or more wires that transmit a driving force generated in the drive unit to the end effector. The elongated portion includes a bending portion in which a plurality of segment pieces arranged in a direction along a center axis of the elongated portion are connected so that the segment pieces adjacent to each other in both directions are pivotable on pivot axes that are twisted relative to each other. The one or more wires are positioned to be distant from the center axis in a radial direction and are arranged to pass through positions that intersect the pivot axes.

According to this embodiment, for one segment piece, a segment piece adjacent in one direction along the center axis of the elongated portion is connected thereto so as to be pivotable about a pivot axis orthogonal to the center axis of the elongated portion, and another segment piece adjacent in another direction is connected thereto so as to be pivotable about a pivot axis that is twisted relative to the aforementioned pivot axis. By repeating this connecting operation, a bending portion that can be bent in multiple directions is configured. Since the wires that transmit a driving force to the end effector at the distal end of the elongated portion are caused to pass through positions that intersect the pivot axes on which the segment pieces are pivotably connected so as to connect the drive unit and the end effector, the path lengths of the wires are rarely affected by pivoting between the segment pieces.

In other words, when adjacent segment pieces are relatively pivoted about one pivot axis, only a bending force acts on the wire, not a tensile or compressive force. Thus, the path length can remain the same. By arranging the wires to pass through the positions that intersect the pivot axes at all pivot axes positions, the path length remains the same with respect to the bending about all of the pivot axes. Thus, even when multiple wires are used, the generation of a difference in path length among the wires is prevented, and degradation of the operability can be prevented.

In the aspect described above, each of the segment pieces may include a cylindrical outer wall portion and through holes through which the one or more wires are passed, the through holes being disposed on a radially inner side of the outer wall portion and at positions that intersect the pivot axes, the through holes extending in a direction along the center axis.

In this manner, the wires can be easily arranged to pass through the positions that intersect the pivot axes by simply causing the wires to sequentially pass through the through holes.

In the aspect described above, the one or more wires may extend in the direction along the center axis and may sequentially pass through the through holes that are arranged to be adjacent in one direction of a circumferential direction about the center axis so as to take a helical form.

In this manner, the wires can be smoothly arranged to have a helical form turning in one direction by merely circumferentially shifting the through holes through which the wires are to be passed In the aspect described above, each of the segment pieces may include a cylindrical inner wall portion arranged to be on the radially inner side of the outer wall portion so as to be concentric with the outer wall portion with a space between the inner wall portion and the outer wall portion, and flat plate-shaped connecting portions that connect the inner wall portion to the outer wall portion near the pivot axes, and the through holes may be formed in the connecting portions.

In this manner, the wires can be disposed in cylindrical gaps between the outer wall portion and the inner wall portions that form a double-tube shape. In addition, spaces on the inner side of the inner wall portion and near the center axis can be secured in the direction along the center axis and continuously throughout the entire length.

REFERENCE SIGNS LIST 1 manipulator
2 elongated portion
3 end effector
4 drive unit (actuator)
5 bending portion
6 segment piece
7 outer wall portion
8 inner wall portion
9 connecting portion
11 through hole (first through hole)
12 through hole (second through hole)
13 wire (first wire)
14 wire (second wire)
A, B pivot axis

The invention claimed is:

1. A manipulator comprising:
an elongated portion;
a bending portion coupled to a distal end of the elongated portion, the bending portion being formed by articulating a plurality of segment pieces;
an end effector coupled to a distal end of the bending portion;
an actuator coupled to a proximal end of the elongated portion;
a first wire coupled between the actuator and the end effector, the first wire being configured to actuate the end effector; and
a second wire coupled between the actuator and the bending portion, the second wire being configured to actuate the bending portion,
wherein:
each of the plurality of segment pieces is configured to be articulated so as to be twisted circumferentially relative to adjacent segment pieces of the plurality of segment pieces about a longitudinal central axis of the bending portion,
the first wire is configured to be inserted into the plurality of segment pieces so as to form a substantially twisted path, and
each of the plurality of segment pieces further comprises a plurality of first through holes through which the first wire is inserted, each of the first through holes extending in a direction of the longitudinal central axis of the bending portion.

2. The manipulator according to claim 1, wherein the first wire is configured to:
extend in the direction of the longitudinal central axis; and
sequentially pass through the plurality of first through holes that are arranged to be adjacent in one direction of a circumferential direction about the longitudinal central axis.

3. The manipulator according to claim 1, wherein each of the plurality of the segment pieces further comprises:
an outer wall portion;
an inner wall portion disposed on the radially inner side of the outer wall portion;
a connecting portion coupled between the outer wall portion and the inner wall portion, and
the plurality of first through holes are disposed on the connecting portion.

4. The manipulator according to claim 1, wherein:
each of the plurality of the segment pieces further comprises a second through hole through which the second wire is inserted, each of the second through holes extending in the direction of the longitudinal central axis of the bending portion, and
the second wire is configured to be inserted into the plurality of segment pieces substantially parallel to the longitudinal central axis of the bending portion.

5. The manipulator according to claim 4, wherein:
each of the plurality of the segment pieces further comprises an outer wall portion; and
the second through hole is disposed on the outer wall portion of each of the plurality of the segment pieces.

* * * * *